United States Patent
Schaefer et al.

(10) Patent No.: US 6,211,397 B1
(45) Date of Patent: Apr. 3, 2001

(54) PROCESS FOR THE PREPARATION OF α-CHLOROMETHYLENE-TRIORGANYLPHOSPHORANE DERIVATIVES

(75) Inventors: Bernd Schaefer, Dierbach; Ernst Buschmann, Ludwigshafen; Gernot Reissenweber, Boehl-Iggelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/199,286

(22) PCT Filed: Sep. 1, 1992

(86) PCT No.: PCT/EP92/02007

§ 371 Date: Mar. 2, 1994

§ 102(e) Date: Mar. 2, 1994

(87) PCT Pub. No.: WO93/05053

PCT Pub. Date: Mar. 18, 1993

(30) Foreign Application Priority Data

Sep. 12, 1991 (DE) ................................ 41 30 296

(51) Int. Cl.$^7$ .................................. C07B 39/00
(52) U.S. Cl. ............... 558/385; 560/219; 568/13; 568/16; 568/303; 568/308; 423/300
(58) Field of Search ............. 558/385; 560/219; 568/13, 16, 303, 308; 423/300

(56) References Cited

U.S. PATENT DOCUMENTS 5,132,448   7/1992   Schaeffer ............... 558/385

OTHER PUBLICATIONS

Houben Weyl, Methoden der Organischen Chemie vol. E1 (1982) 636–39.*
Markl Chem. Ber. 94, 2996 (1961).*
Markl Chem. Ber. 35, 3003 (1962).*
Houben Weyl, Momethoden de Organischen Chemie, vol. E1, Geroge Thieme Verlag 1982, 636–39.*
Mar., Advance Organic Chemistry, 3rd Ed. 1985, 847.*
Houben–Weyl, Methoden der Organischen Chemie, Vol. E1, George Thieme Verlag 1982, —636–639.
G. Markl, Chem. Ber. 94, 2996 (1961).
Denney et al., J. Org. Chem 27, 998 (1962).
G. Markl. Chem. Ber. 35, 3003 (19620.
Braga et al., Synthetic Communications, 19(16), 2877–2883 (1989).

* cited by examiner

*Primary Examiner*—Gary Geist
(74) *Attorney, Agent, or Firm*—Keil & Weinkauf

(57) ABSTRACT

A process for the preparation of α-chloromethylene-triorganylphosphorane derivatives I

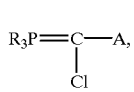
(I)

(radicals R are C-organic substituents and A stands for CN or CO-B where B is a C-organic or O-organic radical which is inert under chlorination conditions) by chlorination of phosphoranes II

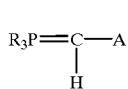
(II)

with chlorine, wherein the chlorination is carried out in the presence of a mineral base as hydrogen chloride acceptor and the chlorine and base are fed to the reaction mixture concurrently but separately at the rates at which they are consumed.

The reaction products I are important intermediates for plant protectants.

7 Claims, No Drawings

PROCESS FOR THE PREPARATION OF α-CHLOROMETHYLENE-TRIORGANYLPHOSPHORANE DERIVATIVES

DESCRIPTION

The present invention relates to an improved process for the preparation of α-chloromethylene-triorganylphosphorane derivatives of the general formula I

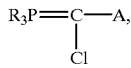
(I)

in which the radicals R can be the same or different and denote C-organic substituents and A stands for cyano or a group CO-B where B denotes a C-organic or O-organic radical which has from 1 to 12 carbon atoms and is inert under chlorination conditions, by chlorination of phosphoranes of formula II

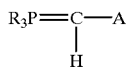
(II)

with chlorine.

It is well known that phosphoranes 11 can be chlorinated to form α-chloromethylene-triphenylphosphorane derivatives (cf Houben-Weyl, *Methoden der Organischen Chemie*, Vol. E1, Georg Thieme Verlag 1982, pp 636–639).

According to G.Märkl [Chem. Ber. 94, 2996 (1961)], one procedure is to chlorinate triphenylphosphine-carbomethoxymethylene (II; A=CO—OCH$_3$) with diluted chlorine gas or with phenyl iodide chloride. The drawback of this method, however, is that the product I can be obtained in a yield of not more than 50%, because phosphonium chloride IIIa

(IIIa), is formed as a by-product.

D. B. Denney and S. T. Ross [*J. Org. Chem.* 27, 998 (1962)] describe two other methods of chlorinating compounds of type II (A=CO—CH$_3$, CO—OC$_2$H$_5$, CO—C$_6$H$_5$) in methylene chloride at from −60° to −70° C., in which the chlorinating agent is a solution of chlorine in carbon tetrachloride.

In the first of these two methods, the chlorination is carried out in the presence of tertiary amines. Apart from the fact that such a method calls for elaborate engineering measures on account of the low temperatures involved, there is the risk of the formation of explosive nitrogen trichloride via a side reaction of the chlorine with the amine.

The second method operates without a base and initially yields the phosphonium chloride of I [(C$_6$H$_5$)$_3$⊕PCH$_2$—A Cl⊖] as a solid, which is then separated, dissolved in water/acetone and converted to I with sodium hydroxide. The fact that two stages are necessary to yield the product makes this method unsatisfactory.

Other known processes [G.Märkl, Chem. Ber. 95, 3003 (1962); J. Bestmann and R. Armsen,*Synthesis*, 590 (1970) and EP-A 421,225] are uneconomical, because they use chlorinating agents which are either expensive [phenyl iodide chloride, sodium p-toluenesulfochloramine (chloramine-T)] or which have to be handled as solids (calcium chloride). Furthermore, their use leads to a high proportion of by-products, which must be disposed of or, if it is desired to recycle them to the process, must be regenerated at high cost.

It was thus an object of the present invention to provide a simple and industrially economical method of synthesizing α-chloromethylene-triorganylphosphorane derivatives I.

Accordingly, a process for the preparation of α-chloromethylene-triorganylphosphorane derivatives of the general formula I

(I)

by chlorination of phosphoranes of formula II

(II)

with chlorine has been found, wherein the chlorination is carried out in the presence of a mineral base as hydrogen chloride acceptor and the chlorine and said base are fed to the reaction mixture concurrently but separately at the rates at which they are consumed.

The process of the invention may be successfully used for the synthesis of all of the α-chloromethylene-triorganylphosphorane derivatives I defined above, particularly those representatives thereof in which A is a group CO-B where B signifies the following:

hydrogen;

a branched or unbranched C$_1$–C$_4$ alkyl group such as methyl, ethyl, n-propyl, isopropyl, n-butyl, sec-butyl, and tert-butyl, where the alkyl group may additionally bear a C$_1$–C$_4$ alkoxy group such as methoxy, ethoxy, isopropoxy, and tert-butoxy;

a cyclopropyl, cyclobutyl, cyclopentyl, or cyclohexyl group;

a branched or unbranched C$_1$–C$_8$ alkoxy group, in particular a C$_1$–C$_6$ alkoxy group, such as methoxy, ethoxy, n-propoxy, 1-methylethoxy, n-butoxy, 1-methylpropoxy, 2-methylpropoxy, 1,1-dimethylethoxy, n-pentoxy, 1-methyl-butoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-i-methylpropoxy, and 1-ethyl-2-methylpropoxy, and preferably methoxy and ethoxy;

a branched or unbranched C$_1$–C$_6$-alkylthio group such as methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1 ,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio, and preferably methylthio and ethylthio;

a $C_1$–$C_6$-alkoxi-$C_1$–$C_6$ alkoxi group, in particular a $C_1$–$C_4$-alkoxy-$C_1$–$C_4$-alkoxy group, such as methoxymethoxy, ethoxymethoxy, n-propoxymethoxy, (1-methylethoxy)methoxy, n-butoxymethoxy, (1-methylpropoxy)methoxy, (2-methylpropoxy)methoxy, (1,1-dimethylethoxy)methoxy, methoxyethoxy, ethoxyethoxy, n-propoxyethoxy, (1-methylethoxy)ethoxy, n-butoxyethoxy, (1-methylpropoxy)ethoxy, (2-methylpropoxy)ethoxy, (1,1-dimethylethoxy)ethoxy, 3-(methoxy)propoxy, 2-(methoxy)propoxy, and 2-(ethoxy)propoxy, and preferably methoxymethoxy;

an aryl group, an aryloxy group, or an aryl-$C_1$–$C_6$-alkoxy group, where in each case the aryl group may be unsubstituted or can bear a phenyl radical or from one to three of the following radicals: $C_1$–$C_4$-alkyl, $C_1$–$C_4$-alkoxy, nitro, trifluoromethyl and/or halo;

in particular the phenyl group, a $C_1$–$C_4$-alkylphenyl group such as o-, m-, p-tolyl, a $C_1$–$C_4$-alkoxyphenyl group such as o-, m-, p-methoxyphenyl, a halophenyl group such as o-, m-, p-fluorophenyl, o-, m-, p-chlorophenyl, and o-, m-, p-bromophenyl, the o-, m-, p-nitrophenyl group, the o-, m-, p-(trifluoromethyl)phenyl group, the o-, m-, p-biphenyl group, the naphthyl group, the phenoxy group, the naphthoxy group, a phenyl-$C_1$–$C_6$-alkoxy group, or a naphthyl-$C_1$–$C_6$-alkyl group, such as benzyloxy, 1-phenylethoxy, 2-phenylethoxy, 1-phenylprop-1-yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 4-phenylbut-2-yloxy, 1-(phenylmethyl)eth-1-yloxy, 1-(phenylmethyl)-1-(methyl)eth-1-yloxy, 1-(phenylmethyl)prop-1-yloxy, naphthylmethyloxy, 1-naphthylethyloxy, 2-naphthylethyloxy, 1-naphthylprop-1-yloxy, 2-naphthylprop-1-yloxy, 3-naphthylprop-1-yloxy, 1-naphthylbut-1-yloxy, 2-naphthylbut-1-yloxy, 3-naphthylbut-1-yloxy, 4-naphthylbut-1-yloxy, 1-naphthylbut-2-yloxy, 2-naphthylbut-2-yloxy, 3-naphthylbut-2-yloxy, 4-naphthylbut-2-yloxy, 1-(naphthylmethyl)eth-1-yloxy, 1-(naphthylmethyl)-1-(methyl)eth-1-yloxy, and 1-(naphthylmethyl)prop-1-yloxy, and preferably phenyl, phenoxy, benzyloxy, 2-phenylethoxy, 2-naphthyl, and 2-naphthylethoxy, and each of said phenyl and naphthyl radicals may additionally carry from 1 to 3 substituents which are inert under the conditions of the reaction.

The radicals R attached to phosphorus may be the same or different and denote, for example, branched or unbranched $C_1$–$C_8$ alkyl groups, $C_5$–$C_6$ cycloalkyl groups, and, in particular, phenyl, which can carry further substituents inert to the conditions of the reaction, for example $C_1$–$C_4$ alkyl such as methyl, ethyl, and tertbutyl, $C_1$–$C_4$ alkoxy such as methoxy, or halogen such as fluorine, chlorine, and bromine. Unsubstituted phenyl radicals are preferred, since the starting compound triphenylphosphine used for the synthesis of the ylids is very cheap and, in addition, the reaction yields solid triphenylphosphine oxide, which is very sluggish to react and is easy to separate.

The phosphoranes II serving as starting materials are known or are obtainable in known manner [cf A. Maercker, Org. Reactions, 14, 402 (1965), Ramirez and Dershowitz, J. Org. Chem. 22, 41 (1957), G. Wittig and W. Haag, Chem. Ber. 88, 1654 (1955), and O.Isler et al, Helv. Chim. Acta 40, 1242 (1957)], in that a tertiary phosphine and a compound Hal—$CH_2$—A are reacted to form a phosphonium salt of formula III

in which Hal denotes halogen, particularly chlorine, and this salt is converted to the phosphorane II by means of a base and without isolation from the reaction mixture.

The reaction takes place in an inert and preferably polar solvent or diluent, advantageously in the same solvent or diluent as is used for the subsequent chlorination of the phosphorane II.

The amount of solvent used should be such as to ensure that the starting materials are completely dissolved. It is normally adequate to use the solvent in an amount which is from 5 to 10 times the amount of the tertiary phosphine.

To ensure complete conversion, it is necessary to use at least equimolar amounts of tertiary phosphine and α-haloacyl derivative, although a slight excess of up to about 10% molar of one or the other of these reactants is acceptable.

In general, atmospheric pressure is employed, and the reaction temperature is generally between 20° C. and the boiling temperature of the solvent used.

Preferably, the phosphorane II is not isolated from the reaction mixture before being subjected to the process of the invention in the same or a different reaction vessel.

Examples of suitable solvents or diluents for the phosphorane II are aromatic hydrocarbons such as benzene, toluene, o-, m-, and p-xylene, and nitrobenzene, chlorinated hydrocarbons such as methylene chloride, chloroform, carbon tetrachloride, 1,2-dichloroethane, chlorobenzene, 1,2-, 1,3-, and 1,4-dichlorobenzenes, and particularly preferred solvents are aliphatic and cycloaliphatic alcohols having from 1 to 6 carbon atoms, such as methanol, ethanol, n-propanol, isopropanol, n-butanol, isobutanol, n-pentanol, n-hexanol, and cyclohexanol.

Mixtures of alcohol and water containing up to about 40% v/v of water, are also well suited for use as solvents.

The amount of solvent used is not crucial and it will, as a rule, be sufficient to use a molar amount of solvent which is from 5 to 10 times that of compound II.

According to the invention, the chlorination takes place in the presence of a mineral base acting as hydrogen chloride acceptor, this being added to the solution of II at the same time as the chlorine and at the rate at which it is consumed.

Chlorination is preferably effected by the use of pure chlorine gas, although it is possible to use liquid chlorine or mixtures of chlorine gas and inert gases such as nitrogen, argon, carbon dioxide, and steam. In such cases the proportions of the components of the mixture are suitably from 5 to 50 moles of chlorine per mole of inert gas.

To achieve complete conversion, at least 1.0 mole of chlorine ($Cl_2$) will be required for each mole of phosphorane II. It is preferred to use equimolar amounts or slightly more or less than the molar amount (up to ca 10% molar) relevant to II.

Suitable mineral bases are salts of weak acids with alkali metals, alkaline-earth metals, or transition metals, which salts react as a base in aqueous solution. Such salts are, primarily, alkali metal and alkaline-earth metal hydroxides, such as lithium hydroxide, sodium hydroxide, potassium hydroxide, calcium hydroxide, and magnesium hydroxide, alkaline-earth metal oxides such as magnesium oxide, and alkali metal and alkaline-earth metal salts of weak organic acids such as carbonic acid, acetic acid, and benzoic acid, eg, sodium carbonate, potassium carbonate, calcium carbonate, sodium bicarbonate, sodium acetate, and potassium acetate.

Particularly preferred mineral bases are the alkali metal hydroxides, and especially sodium hydroxide and potassium hydroxide.

The mineral base can be used in the form of a suspension or, preferably, an aqueous solution. The amount used is advantageously such that the pH of the reaction mixture does not rise above 9 and is preferably between 7 and 8, throughout the reaction. As a rule, 2 equivalents of base per mole of phosphorane II suffice.

The reaction temperature is generally between −50° and +50° C., preferably between −15° and +30 C.

No special pressure conditions are necessary, and it will therefore be usual to carry out the reaction at atmospheric pressure. It is possible to use a slightly reduced or slightly elevated pressure, but not, normally, to any advantage.

The product is worked up in the usual manner, for example by extraction or filtration. However, it will normally be recommendable to subject the products I to further reaction without removing them from the reaction mixture. It is preferred to react them with a carbonyl compound of formula IV

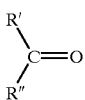

(IV)

in which R' and R" independently denote hydrogen or c-organic radicals [cf, eg, G.Märkl, Chem. Ber. 94, 2996 (1961), EP-A 207,894, EP-A 340,708, EP-A 384,199, the Japanese Laid-open Patent Application 155,358/84, and the Japanese Patent Kokai 152,465/1985] to give the corresponding olefinically unsaturated compound of formula V

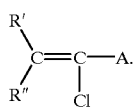

(V)

Particularly preferred carbonyl compounds IV are benzaldehyde, nitrobenzaldehyde, and aminobenzaldehyde, 1,2,3,4-tetrahydrophthalimidobenzaldehyde, 3-chloro-2-(3-formylphenyl)-4,5,6,7-tetrahydroimidazole and the mono- and dihalogenated derivatives thereof.

The α-chloromethylene-triorganylphosphorane derivatives I which are made available by the process of the invention in a simple manner and in good yields are valuable intermediates for the synthesis of plant protectants and pharmaceuticals. They are particularly useful for the synthesis of cinnamates VI, which are important starting points for herbicides and growth regulators (cf, eg, EP-A 300,387 and EP-A 240,659):

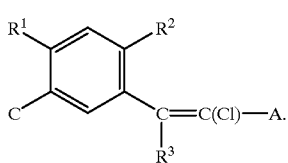

(VI)

In the above formula VI, C denotes the nitro group, the amino group or a protected amino group such as 1,2,3,4-tetrahydrophthalimido, $R^1$ denotes hydrogen or halogen, preferably fluorine, $R^2$ denotes halogen, preferably chlorine, and $R^3$ denotes hydrogen or $C_1$–$C_4$ alkyl.

EXAMPLE 1

Methyl 2,α-dichloro-5-nitrocinnamate

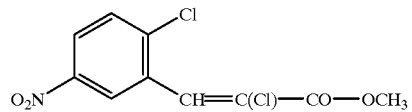

a) Preparation of phosphorane II:

A solution of 157 g (0.6 mole) of triphenylphosphine and 68.4 g (0.59 mole) of methyl chloroacetate in 150 ml of methanol was heated at the boil for 2 hours. To the resulting mixture there were added, at 20–25° C., 1050 ml of methanol and 25 ml of 25% w/w aqueous caustic soda.

b) Chlorination of phosphorane II:

42 g (0.59 mole) of chlorine gas were passed through the above solution with slight cooling to 15–20° C., whilst the pH was kept at about 7.4 by simultaneously metering in 25% w/w aqueous caustic soda. On completion of the feed of chlorine gas, the reaction mixture was stirred for a further hour. The α-chloromethoxycarbonylmethylene triphenylphosphorane thus obtained may be used in situ for further syntheses.

c) Reaction of α-chloromethoxycarbonylmethylene-tripheaylphosphorane with 2-chloro-5-nitrobenzaldehyde:

To the reaction mixture obtained above, cooled slightly to 15–20° C., there were added, portionwise, 102 g (0.55 mole) of 2chloro-5-nitrobenzaldehyde. The mixture was stirred for 2 hours at 20–25° C. and hydrolysis was carried out by the addition of 300 ml of water, after which the resulting solids were filtered off, washed twice with 100 ml of water each time and twice with 100 ml of methanol each time, followed by drying under reduced pressure at 50° C. Yield: 75% of methyl 2,α-dichloro-3-nitrocinnamate, mp 110–112° C.

EXAMPLE 2

Ethyl α-chloro-4-nitrocinnamate

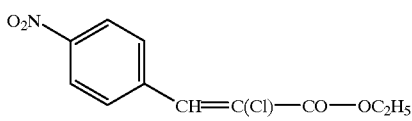

In a manner similar to that described in Example 1, α-chloroethoxycarbonyl-methylene-triphenylphosphorane was synthesized from 157 g (0.6 mole) of triphenylphosphine and 72.3 g (0.59 mole) of ethyl chloroacetate in ethanol and then chlorinated. To make ethyl α-chloro-4-nitrocinnamate, the resulting reaction mixture was reacted with 83.1 g (0.55 mole) of 4-nitrobenzaldehyde in a manner analogous to that described in Example 1. Yield: 86%, mp 108–110° C.

EXAMPLE 3

Ethyl 2,α-dichloro-5-nitrocinnamate

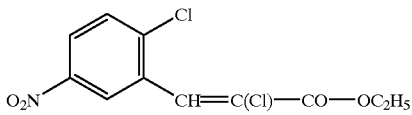

a) Synthesis of phosphorane II:

A solution of 157 g (0.6 mole) of triphenylphosphine and 72.3 g (0.59 mole) of ethyl chloroacetate in 150 ml of ethanol was heated at the boil for 2 hours. To the resulting mixture there were added, at 20–25° C., 800 ml of ethanol, 200 ml of water, and 10 ml of 50% w/w aqueous caustic soda.

b) Chlorination of phosphorane II:

42 g (0.59 mole) of chlorine gas were passed through the above solution with slight cooling to 15–20° C., whilst the pH was kept at about 7.4 by simultaneously metering in 25% w/w aqueous caustic soda. On completion of the feed of chlorine gas, the reaction mixture was stirred for a further hour. The α-chloroethoxycarbonylmethylene-triphenylphosphorane thus obtained may be used in situ for further syntheses.

c) Reaction of α-chloroethoxycarbonylmethylene-triphenylphosphorane with 2-chloro-5-nitrobenzaldehyde:

To the reaction mixture obtained above, cooled slightly to 15–20° C,. there were added, portionwise, 102 g (0.55 mole) of 2-chloro-5-nitrobenzaldehyde. The mixture was stirred for 2 hours at 20–25° C. and hydrolysis was then carried out by the addition of 120 ml of water, after which the resulting solids were filtered off, washed twice with 100 ml of water each time and twice with 100 ml of methanol each time, followed by drying under reduced pressure at 50° C. Yield: 88% of methyl 2,α-dichloroethoxycarbonyl, mp 96–98° C.

What is claimed is:

1. A process for the preparation of α-chloromethylene-triorganylphosphorane derivatives of the formula I

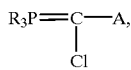
(I)

in which the radicals R can be the same or different and denote C-organic substituents and A stands for cyano or a group CO-B where B is a C-organic or O-organic radical which has from 1 to 12 carbon atoms and is inert under chlorination conditions, by chlorination of phosphoranes of formula II

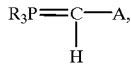
(II)

with chlorine, wherein the chlorination is carried out in the presence of an alkali metal hydroxide as hydrogen chloride acceptor and the chlorine and said base are fed to the reaction mixture concurrently but separately at the rates at which they are consumed, such that the pH does not rise above 9 throughout the reaction.

2. A process as defined in claim 1, wherein the starting material is a mixture of phosphorane II and an inert solvent such as is obtained when said II is synthesized from a tertiary phosphine and a compound of the structure Hal—CH$_2$—A, where Hal denotes halogen, with subsequent reaction of the resulting phosphonium salt with a base.

3. A process as defined in claim 1, wherein the chlorination is carried out using undiluted chlorine gas.

4. A process as defined in claim 1, wherein the chlorination is carried out in a lower alcohol acting as solvent.

5. A process for the preparation of olefinically unsaturated compounds of formula V

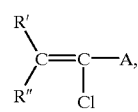
(V)

in which R' and R" denote hydrogen or C-organic radicals which comprises: reacting a α-chloromethylene-triorganylphosphorane derivative I

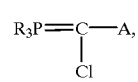
(I)

in which the radicals R can be the same or different and denote C-organic substituents and A stands for cyano or a group CO-B where B is a C-organic or O-organic radical which has from 1 to 12 carbon atoms and is inert under chlorination conditions, with a carbonyl compound IV

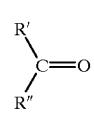
(IV)

wherein the derivative I is present in the reaction mixture formed by the process defined in claim 1.

6. A process for the preparation of olefinically unsaturated compounds of formula V

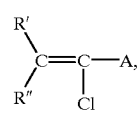
(V)

in which R' and R" denote hydrogen or C-organic radicals, by the reaction of a α-chloromethylene-triorganylphosphorane derivative I

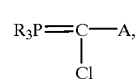
(I)

in which the radicals R can be the same or different and denote C-organic substituents and A stands for cyano or a group CO-B where B is a C-organic or O-organic radical which has from 1 to 12 carbon atoms and is inert under chlorination conditions, with a carbonyl compound IV

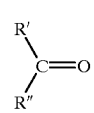
(IV)

wherein the derivative I is present in the reaction mixture formed by the process defined in claim 2.

7. A process as defined in claim 1, wherein the alkali metal hydroxide is sodium hydroxide.

* * * * *